US00PP10365P

United States Patent [19]

Utecht

[11] Patent Number: Plant 10,365

[45] Date of Patent: Apr. 28, 1998

[54] GERANIUM PLANT NAMED 'FISROCK'

[75] Inventor: Angelika Utecht, Montabaur, Germany

[73] Assignee: Florfis AG, Binningen, Switzerland

[21] Appl. No.: 754,365

[22] Filed: Nov. 22, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITM UPOVROM Citation for DE PBR PEl 00999 for 'Fisrock', Dec. 18 1995.

GTITM UPOVROM Citation CA PBR 96–795 for 'Fisrock', Jul. 29, 1996.

*Primary Examiner*—James R. Feyrer

*Attorney, Agent, or Firm*—Foley & Lardner

[57] ABSTRACT

A new and distinct cultivar of geranium plant named 'Fisrock', particularly characterized by the combined features of dark-red double flowers, comparatively dark green foliage with distinct zonation, medium long, well branched plant habit, and early to medium spring flower response.

1 Drawing Sheet

The present invention comprises a new and distinct cultivar of geranium, botanically known as *Pelargonium peltatum*, and hereinafter referred to by the cultivar name 'Fisrock'.

'Fisrock' is a product of planned breeding program which had the objective of creating new ivy geranium cultivars with red flower color, zoned foliage, moderately vigorous growth, and hopefully an improvement with respect to those characteristics over the cultivar 'Fisrom', disclosed in U.S. Plant Pat. No. 7,567.

'Fisrock' was originated from a hybridization made by the inventor Angelika Utecht in a controlled breeding program in Galdar, Gran Canaria, Spain, in 1991. The female parent was the light violet flowering variety 'Fisam', disclosed in U.S. Plant Pat. No. 8,327, having double flowers, medium green zoned foliage and a medium long, well branched plant habit. The male parent of 'Fisrock' was 'Guishiva', a cultivar having deep red semi-double flowers, comparatively dark green zoned foliage, and compact and bushy plant habit.

'Fisrock' was discovered and selected as one flowering plant within the progeny of the stated cross by Angelika Utecht in 1992 in a controlled environment in Galdar, Gran Canaria, Spain. The first act of asexual reproduction of Fisrock was accomplished when vegatative cuttings were taken from the initial selection in Autumn 1992 in a controlled environment in Galdar, Gran Canaria, Spain, by or under the supervision of, Angelika Utecht.

Horticultural examination of plants grown from these cuttings, initiated in May 1993 in Hillscheid, Federal Republic of Germany, and continuing thereafter, has demonstrated that the combination of characteristics as herein disclosed for 'Fisrock' are firmly fixed and are retained through successive generations of asexual reproduction.

'Fisrock' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany, under greenhouse conditions which approximate those generally used in commercial practice.

The following traits have been repeatedly observed and are determined to be basic characteristics of 'Fisrock', which in combination distinguish this geranium as a new and distinct cultivar:

1. Intense dark red flower color
2. Double flower form
3. Very dark green foliage for an ivy geranium
4. Medium to strong zonation
5. Medium, well-branched plant habit
6. Early to medium spring flower response Of the many commercial cultivars known to the present inventor, the most similar in comparison to 'Fisrock' are the parent 'Fisrom' and the parent cultivar 'Gushiva'. Reference is made to attached Chart A which compares certain characteristics of 'Fisrock' to those same characteristics of 'Fisrom'.

In general, comparison to 'Fisrom', 'Fisrock' has smaller flowers with a darker red shade of color, and darker green, more distinctly zoned foliage. In comparison to 'Guishiva', 'Fisrock' has double, fuller and more round shaped florets, a darker red shade of flower color, and more vigorous growth. The plant habit of 'Fisrock' is intermediate, being longer trailing than 'Guishiva' but more compact and bushier than 'Fisrom'.

The accompanying photographic drawing shows typical flower and foliage characteristics of Fisrock, with colors being as true as possible to illustrations on this type.

In the following description color references are made to The Royal Horticultural Society Color Chart. The color values were determined indoors from flowers taken from plants grown in a greenhouse in May 1995 in Hillscheid, Germany.

Classification:

*Botanical.*—A hybrid of the species *Pelargonium peltatum l'hert.*

*Commercial.*—Ivy geranium, cv. 'Fisrock'.

Inflorescence

Umbel:

*Shape.*—Generally semi-spherical.

*Average diameter.*—95 mm.

*Peduncle length.*—173 mm.

*Pedicel length.*—27 mm.

*Pedicel color.*—Upper part dark red.

*Number of flowers per umbel.*—12

Corolla:

*Average diameter.*—47 mm.

*Form.*—Double.

*Number of petals.*—13.

*Number of petaloids.*—2–3.

*Color (general tonality from a distance of three meters)* .—Dark red.

*Color of upper petals.*—46 A-B.

*Markings on upper petals.*—2 black veins, not visible in photographic drawing.

*Color of lower petals.*—46 A-B.

*Color of lower surface of petals.*—53 C.

*Number of sepals.*—5.

*Color of sepals.*—Medium green.

Bud:

*Shape.*—Elliptical.

*Color (adaxial).*—Medium green.

*Color (abaxial).*—Purple red.

Reproductive organs:

*Androecium.*—2–3 fertile anthers, white filaments, orange pollen.

*Gynoecium.*—5–6-lobed stigma, purple violet with white filaments.

*Seed set.*—No seed set observed.

Spring flowering response period: In Hillscheid, Germany, in 1995 plants had on average 0.4 flowers opened 15 weeks after planting of unrooted cuttings (pinched plants).

Outdoor flower production: The flower count in 1994 in Hillscheid, Germany indicated about 70 umbels per plant for May through August observation period.

Durability: Good shatter resistance.

Plant

Foliage:

*Form.*—Ivy shaped.

*Margin.*—Entire.

*Size of leaf.*—75 mm.

*Color of upper surface.*—Medium dark green, approximately 137A-B.

*Color of zonation.*—Brown, about 166 A.

*Tolerance of botrytis.*—Average.

General appearance and form:

*Internode length.*—40 mm.

*Branching pattern.*—7.2 branches after 16 weeks.

*Length of plants.*—75 cm (in September, based on 35-week-old plant).

CHART A

| | FISROCK | FISROM |
|---|---|---|
| Flower color: | 46 A-B | 46 B |
| Diameter of flower: | 47 mm | 53 mm |
| Color of foliage: | Medium to dark green 137 A-B | Medium green 137 B-C |
| Zonation | Medium to strong | very weak |
| Growth/Plant Habit: | Medium 75 cm | Long trailing 105 cm |

I claim:

1. A new and distinct cultivar of geranium plant named 'Fisrock', as illustrated and described.

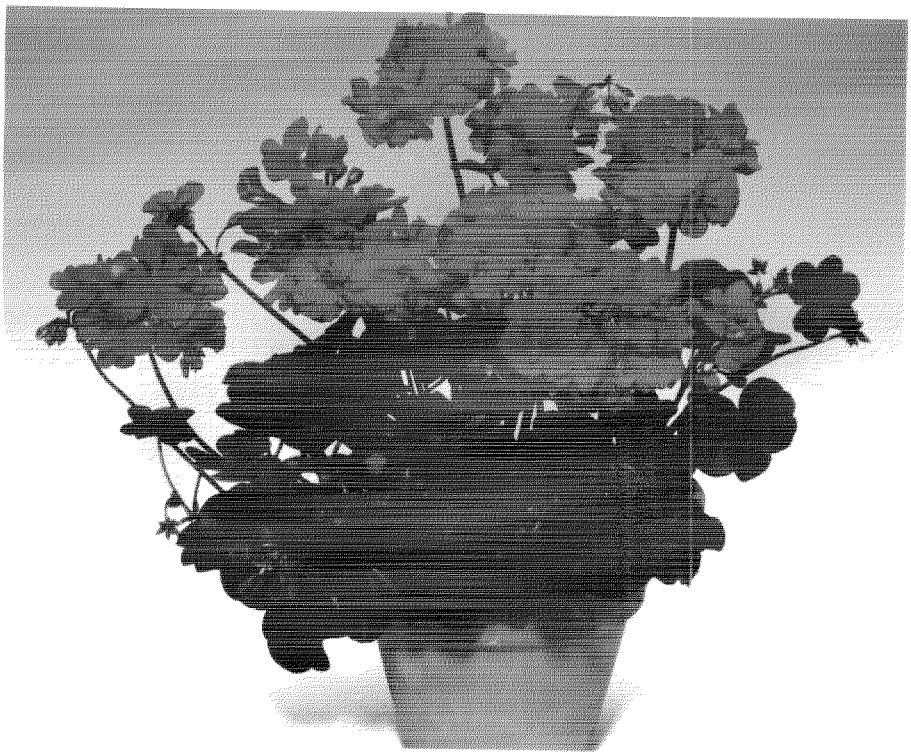

* * * * *